US011312995B2

(12) United States Patent
Chang et al.

(10) Patent No.: US 11,312,995 B2
(45) Date of Patent: Apr. 26, 2022

(54) METHOD FOR DETECTING SNP SITE ON SMA GENE

(71) Applicant: Feng Chi Biotech Corporation, Taipei (TW)

(72) Inventors: Hung Ming Chang, Taipei (TW); Chien Hsing Lin, Taipei (TW); Shu Ming Chang, Taipei (TW)

(73) Assignee: FENG CHI BIOTECH CORPORATION, Taipei (TW)

( * ) Notice: Subject to any disclaimer, the term of this patent is extended or adjusted under 35 U.S.C. 154(b) by 195 days.

(21) Appl. No.: 16/210,986

(22) Filed: Dec. 5, 2018

(65) Prior Publication Data
US 2019/0360046 A1 Nov. 28, 2019

(30) Foreign Application Priority Data

May 25, 2018 (TW) .................................. 10711802

(51) Int. Cl.
*C12Q 1/6883* (2018.01)
(52) U.S. Cl.
CPC ..... *C12Q 1/6883* (2013.01); *C12Q 2600/156* (2013.01)
(58) Field of Classification Search
None
See application file for complete search history.

(56) References Cited

U.S. PATENT DOCUMENTS

| 10,494,682 | B2 * | 12/2019 | Wittwer | ................ | C12Q 1/686 |
| 2004/0110200 | A1 * | 6/2004 | Peoples | ................ | C12Q 1/6827 |
| | | | | | 506/9 |
| 2014/0199695 | A1 * | 7/2014 | Edelmann | ............ | C12Q 1/6883 |
| | | | | | 435/6.11 |
| 2016/0152950 | A1 * | 6/2016 | Zhang | ................ | C12N 5/0619 |
| | | | | | 435/368 |

FOREIGN PATENT DOCUMENTS

| TW | 201007167 | * | 2/2010 |
| TW | 201007167 | A | | 2/2010 |

OTHER PUBLICATIONS

Li (Electrophoresis 1999 vol. 20 pp. 1258-1265).*
Masouleh (Plant Biotechnology Journal 2009 vol. 7 pp. 355-363).*
Mehta (Int J Legal Med 2017 vol. 131 pp. 21-37).*
Kao, et al.; "Determination of SMNI / SMN2 Gene Dosage by a Quantitative Genotyping Platform Combining Capillary Electrophoresis and MALDI -TOF Mass Spectrometry" Clinical Chemistry, 2006, 52:3, pp. 361-369, Cited in communication issued in a counterpart foreign application.
Niba et al.; "SMA Diagnosis: Detection of SMNI Deletion with Real-Time mCOP-PCR System Using Fresh Blood DNA", Kobe J Med Sci., vol. 63, No. 3, pp. E80-E83, 2017; Cited in communication issued in a counterpart foreign application.
Hahner et al.; "Strategies for SNP genotyping by mass spectrtrometry", International Congress Series, pp. 11-16, 2003, Cited in communication issued in a counterpart foreign application.

* cited by examiner

*Primary Examiner* — Amanda Haney
(74) *Attorney, Agent, or Firm* — Hamre, Schumann, Mueller & Larson, P.C.

(57) ABSTRACT

A method for detecting a SNP site on a SMA gene is disclosed, and includes steps of: (S10) performing a PCR for amplifying a nucleic a nucleic acid fragment containing a SNP site; (S20) performing a dephosphorylation reaction on the nucleic acid fragment; (S30) performing an extension reaction on the nucleic acid fragment, wherein the SNP site is identified by using an extension primer, a 3'-end of the extension primer is extended by a single nucleotide which is complementary to a base of the SNP site, and thus an extended extension primer is obtained; (S40) performing a purification reaction; and (S50) measuring a molecular weight of the extended extension primer, and determining a type of a base of the single nucleotide based upon the molecular weight, thereby determining whether deletion occurs to the SNP site.

1 Claim, 7 Drawing Sheets
Specification includes a Sequence Listing.

METHOD FOR DETECTING SNP SITE ON SMA GENE

CROSS REFERENCE TO RELATED APPLICATIONS

This application claims priority to Taiwan Application Serial Number 107118029, filed on May 25, 2018, which is herein incorporated by reference.

INCORPORATION BY REFERENCE OF MATERIAL IN ASCII TEXT FILE

This application incorporates by reference the Sequence Listing contained in the following ASCII text files submitted herewith:

Filename: Seq Listing20211123.txt, created on Nov. 23, 2021, 5,601 bytes in size.

FIELD OF THE INVENTION

The present disclosure relates to a method for detecting a genetic defect, and in particular to a method for detecting a single nucleotide polymorphism (SNP) site on spinal muscular atrophy (SMA) genes.

BACKGROUND OF DISCLOSURE

The cause of spinal muscular atrophy (SMA) is the genetic defect that leads to degeneration and loss of the motor neurons in the anterior horn of the spinal cord, resulting in progressive weakness and paralysis of the muscles, accompanied by the muscle atrophy symptom. The muscle atrophy is symmetrical, wherein the lower limbs have more severity than the upper limbs, and the proximal ends of the body are more susceptible than the distal ends. There is no treatment so far. SMA is classified into three types according to severity:

Severe spinal muscular atrophy (SMA type I): About one in 20,000 infants suffers from this disorder type, which is the most common type. When the infants in the uterus or within three months after birth suffer from the symptoms, such as limb weakness, crying weakness and a difficulty in breathing. Since the patients are susceptible to respiratory diseases, they may die of pneumonia in the first year of life. The patients rarely live beyond three years of age without actively supportive respiratory therapy.

Intermediate type (SMA type II): The symptoms often appear in the period from half a year to one year after birth. The patients exhibit symmetrical weakness in the lower limbs, are unable to stand or walk, have diminished tendon reflexes, and occasionally have trembling tongue or hands. A quarter of the patients often die of respiratory infections before the age of two years. Other survivors need supportive respiratory therapy to maintain life, possibly because scoliosis, caused by continuous muscle weakness, affects lung function and causes a difficulty in breathing.

Mild spinal muscular atrophy (Kugelberg-Welander Disease, SMA type III): The symptoms may appear at uncertain time, and may appear from one year old to adolescent or adult. The symptoms are symmetrical mild muscle weakness of the proximal ends of the low limbs, and inconvenience in climbing stairs, walking and running. The patients' long-term survival is fairly good.

The incidence of spinal muscular a trophy approximately ranges from 1/1,000 to 1/25,000. Domestic eugenics outpatient clinics have found family cases that family members successively suffer from this disorder. In Taiwan, there are about 30 new cases in 300,000 newborn infants per year. 90 to 95% patients of spinal muscular atrophy are caused by homozygous deletion of the survival motor neuron 1 (SMN1) gene.

The current method for detecting defects in the SMN1 gene is based upon the quantitative polymerase chain reaction (known as the real-time PCR) or the gene sequencing. However, no matter what method is used, there are issues, such as low sensitivity, high cost, and poor efficiency. Therefore, it is necessary to develop a solution to the above problem.

SUMMARY OF INVENTION

An object of the present disclosure is to provide a method for identifying homozygous deletion on a survival motor neuron 1 (SMN1) gene. The method of the present disclosure (1) simultaneously detect a plurality of single nucleotide polymorphism (SNP) sites in the same reaction, greatly reducing the analysis cost; (2) is simple and rapid, and is applicable to various specimens, such as fresh tissue, frozen tissue, formalin-fixed paraffin-embedded (FFPE) tissue, genomic DNA extracted from cell lines, or plasma circulating cell-free DNA, etc. (3) Since the SNP sites (loci) are located in the region of the SMN1 gene where deletion occurs with high possibility, the deletion on the SMN1 gene can be confirmed by detecting the SNP sites, the deletions in different sizes in tiny amounts of specimens can also be accurately detected, and the method of the present disclosure is greatly efficient. (4) Since the deletion on the SMN1 gene is highly correlated with spinal muscular atrophy (SMA), quickly identifying the genotypes of the SMA genes of the patients by the method of the present disclosure is valuable for the study of spinal muscular atrophy.

To achieve the above object and to solve the problems in the prior art, the present disclosure provides a method for detecting a single nucleotide polymorphism (SNP) site on a spinal muscular atrophy (SMA) gene, comprising steps of:

(S10) performing a polymerase chain reaction (PCR) on a specimen, wherein a nucleic acid fragment containing a SNP site in the specimen is amplified by using a pair of amplification primers to obtain an amplified nucleic acid fragment;

(S20) performing a dephosphorylation reaction on the amplified nucleic acid fragment to remove a phosphate at a 5' end of the nucleic acid fragment in the PCR;

(S30) performing an extension reaction on the amplified nucleic acid fragment, wherein the SNP site is identified by using an extension primer, a 3'-end of the extension primer is extended by a single nucleotide which is complementary to a base of the SNP site, and thus an extended extension primer is obtained;

(S40) performing a purification reaction to purify the extended extension primer; and (S50) measuring a molecular weight of the extended extension primer, and determining a type of a base of the single nucleotide based upon the molecular weight, thereby determining whether deletion occurs to the SNP site;

wherein the extension primer comprises one selected from the group consisting of SEQ ID NO:3, SEQ ID NO:6, SEQ ID NO:9 and SEQ ID NO: 12.

In an embodiment of the present disclosure, the pair of amplification primers comprises one pair selected from the group consisting of SEQ ID NO: 1 and SEQ ID NO: 2; SEQ ID NO: 4 and SEQ ID NO: 5; SEQ ID NO: 7 and SEQ ID NO: 8; and SEQ ID NO:10 and SEQ ID NO: 11.

In an embodiment of the present disclosure, a 5'-end of the amplification primer is added with a TAG nucleic acid fragment which is not complementary to the nucleic acid fragment containing the SNP site for increasing a molecular weight difference between the amplification primers and the extension primer.

In an embodiment of the present disclosure, the TAG nucleic acid fragment comprises SEQ ID NO: 19.

In an embodiment of the present disclosure, in the step (S50), measuring the molecular weight of the extended extension primer by using a mass spectrometer, and determining the type of the base of the single nucleotide based upon the molecular weight, thereby determining whether deletion occurs to the SNP site of a survival motor neuron 1 (SMN1) gene.

In an embodiment of the present disclosure, in the step (S50), measuring the molecular weight of the extended extension primer by using a fluorescent electrophoresis, then detecting a type of a labeled fluorescent light of the extended extension primer, and determining the type of the base of the single nucleotide based upon the molecular weight and the type of the fluorescent light, thereby determining whether deletion occurs to the SNP site of a survival motor neuron 1 (SMN1) gene.

In an embodiment of the present disclosure, in the step (S50), when the type of the base of the single nucleotide corresponding to the SNP site is single, the deletion occurs to the SNP site; and when the type of the base of the single nucleotide corresponding to the SNP site is two, no deletion occurs to the SNP site of a survival motor neuron 1 (SMN1) gene.

The present disclosure provides a method for detecting a plurality of single nucleotide polymorphism (SNP) sites on a spinal muscular atrophy (SMA) gene, comprising steps of:

(S100) performing a polymerase chain reaction (PCR) on a specimen, wherein a plurality of nucleic acid fragments, each of which contains a SNP site, in the to-be-tested specimen are amplified by using a plurality of pairs of amplification primers to obtain a plurality of amplified nucleic acid fragments;

(S200) performing a dephosphorylation reaction on the amplified nucleic acid fragments to remove a phosphate at a 5' end of each of the amplified nucleic acid fragment in the PCR;

(S300) performing an extension reaction on the amplified nucleic acid fragments, wherein the SNP sites are identified by using a plurality of extension primers, 3'-end of each of the extension primers is extended by a single nucleotide which is complementary to a base of the corresponding SNP site, and thus a plurality of extended extension primers are obtained;

(S400) performing a purification reaction to purify the extended extension primers; and (S500) measuring molecular weights of the extended extension primers, and determining a types of bases of the single nucleotides based upon the molecular weights, thereby determining whether deletion occurs to the SNP sites;

wherein the extension primers comprise at least two selected from the group consisting of SEQ ID NO:3, SEQ ID NO:6, SEQ ID NO:9 and SEQ ID NO: 12.

In an embodiment of the present disclosure, the pairs of amplification primers comprise at least two pairs selected from the group consisting of SEQ ID NO: 1 and SEQ ID NO: 2; SEQ ID NO: 4 and SEQ ID NO: 5; SEQ ID NO: 7 and SEQ ID NO: 8; and SEQ ID NO:10 and SEQ ID NO: 11.

In an embodiment of the present disclosure, a 5'-end of each of the amplification primers is added with a TAG nucleic acid fragment which is not complementary to the nucleic acid fragments containing the SNP sites for increasing molecular weight differences between the amplification primers and the extension primers.

In an embodiment of the present disclosure, the TAG nucleic acid fragment comprises SEQ ID NO: 19.

In an embodiment of the present disclosure, in the step (S50), measuring the molecular weights of the extended extension primers by using a mass spectrometer, and determining the types of the bases of the single nucleotides based upon the molecular weights, thereby determining whether deletion occurs to the SNP sites of a survival motor neuron 1 (SMN1) gene.

In an embodiment of the present disclosure, in the step (S50), measuring the molecular weights of the extended extension primers by using a fluorescent electrophoresis, then detecting types of labeled fluorescent lights of the extended extension primers, and determining the types of the bases of the single nucleotides based upon the molecular weights and the types of the fluorescent lights, thereby determining whether deletion occurs to the SNP sites of a survival motor neuron 1 (SMN1) gene.

In an embodiment of the present disclosure, in the step (S50), when the type of the base of the single nucleotide corresponding to the SNP site is single, the deletion occurs to the SNP site; and when the type of the base of the single nucleotide corresponding to the SNP site is two, no deletion occurs to the SNP site of a survival motor neuron 1 (SMN1) gene.

In an embodiment of the present disclosure, the number of the SNP sites are four.

In an embodiment of the present disclosure, if the deletion occurs to at least one of the four SNP sites, homozygous deletion occurs to a survival motor neuron 1 (SMN1) gene or the survival motor neuron 2 (SMN2) gene.

In an embodiment of the present disclosure, if the deletion occurs to all of the four SNP sites on a survival motor neuron 1 (SMN1) gene, the to-be-tested specimen is determined to be derived from a patient with spinal muscular atrophy.

BRIEF DESCRIPTION OF DRAWINGS

FIG. 3A to FIG. 3C are mass spectrometry spectrums showing detection of a SNP site on exon 7 of the SMA genes from a negative control group and to-be-tested specimens, by using the extension primer SEQ ID NO: 3 according to an embodiment of the present disclosure, wherein FIG. 3A shows the spectrum from the negative control group, and FIG. 3B and FIG. 3C show the spectrums from the to-be-tested specimens.

FIG. 4A to FIG. 4B are mass spectrometry spectrums showing detection of a first SNP site on intron 7 of the SMA genes from a positive control group and a to-be-tested specimen, by using the extension primer SEQ ID NO: 6 according to an embodiment of the present disclosure, wherein FIG. 4A shows the spectrum from the positive control group, and FIG. 3B shows the spectrum from the to-be-tested specimen.

DETAILED DESCRIPTION OF PREFERRED EMBODIMENTS

Figure 1:
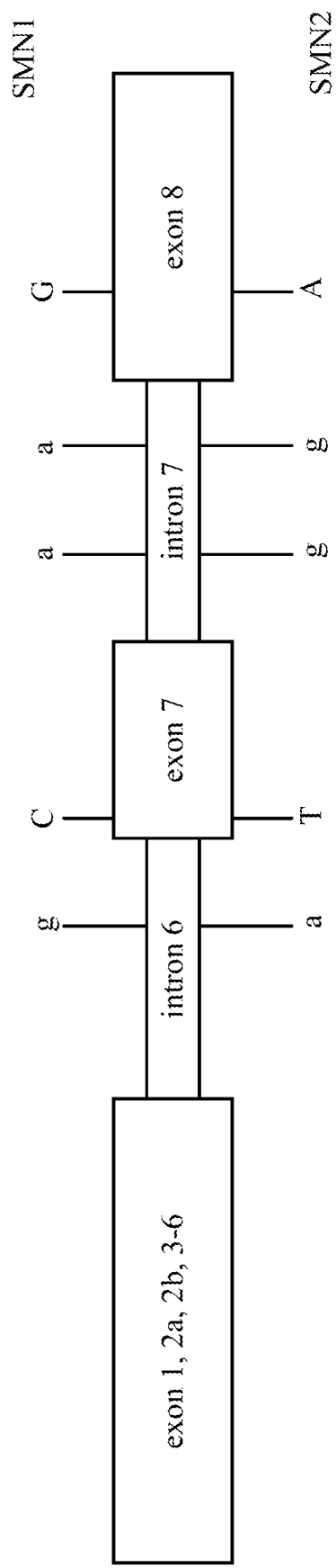
FIG. 1 is a schematic diagram of single nucleotide polymorphism (SNP) sites of the spinal muscular atrophy (SMA) genes.

Refer to FIG. 1, which is a schematic diagram of single nucleotide polymorphism (SNP) sites of the spinal muscular atrophy (SMA) genes. The SMA genes include two genes, the survival motor neuron (SMN1) gene and the survival motor neuron 2 (SMN2) gene. Both genes encode the SMN protein. However, there are five nucleotide differences in the sequences between the SMN1 gene and the SMN2 gene. The five nucleotide differences in the sequences referred to as single nucleotide polymorphism (SNP) sites, as shown in FIG. 1, are respectively located on intron 6, exon 7, intron 7, and exon 8.

For intron 6, the base of the SNP site on the SMN1 gene is guanine (G), and the base of the SNP site on the SMN2 gene is adenine (A). For the exon 7, the base of the SNP1 site on the SMN1 gene is cytosine (C), and the base of the SNP site on the SMN2 gene is thymine (T). For intron 7, the base of the first SNP site on the SMN1 gene is adenine (A), the base of the second SNP site on the SMN1 is adenine (A), the base of the first SNP site on the SMN2 gene is guanine (G), and the base of the second SNP site on SMN2 gene is guanine (G). For exon 8, the base of the SNP site on the SMN1 gene is guanine (G), the base of the SNP site on the SMN2 gene is adenine (A).

Although there are only five nucleotide differences in the sequences between the SMN1 gene and the SMN2 gene, there is a significant difference between the SMN proteins expressed by the SMN1 gene and the SMN proteins expressed by the SMN2 gene. The SMN1 gene expresses a full-length stable SMN protein, whereas only about 15% of the protein expressed by the SMN2 gene is a full-length stable SMN protein, and about 85% is a truncated unstable SMN protein. Therefore, only the protein expressed by the SMN1 gene has a biological significance, but the protein expressed by the SMN2 gene does not. When the SMN1 gene is defective, it is highly likely to cause spinal muscular atrophy. When the SMN2 gene is defective, it basically does not cause disorder.

The typical defect of the SMN1 gene is a wide range of deletion occurring to exon 7, intron 7, and exon 8, leading to the disappearance of the four SNP sites located thereon. The detection method determines whether the homozygous deletion occurs to the SMN1 gene by detecting the absence of the four SNP sites, and, thus, is very valuable for the study of spinal muscular atrophy.

Figure 2:
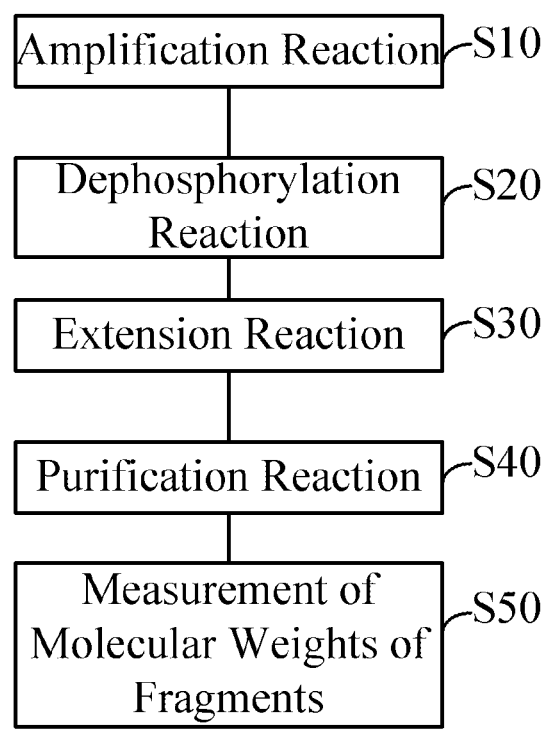
FIG. 2 is a step flowchart in accordance with an embodiment of the present disclosure.

Refer to FIG. 2, which is a step flowchart in accordance with an embodiment of the present disclosure. A method for detecting a single nucleotide polymorphism (SNP) site on spinal muscular atrophy (SMA) genes, includes steps of: (S10) performing a polymerase chain reaction (PCR) on a specimen, wherein a nucleic acid fragment containing a SNP site in the specimen is amplified by using a pair of amplification primers to obtain an amplified nucleic acid fragment; (S20) performing a dephosphorylation reaction on the amplified nucleic acid fragment to remove a phosphate at a 5' end of the nucleic acid fragment in the PCR; (S30) performing an extension reaction on the amplified nucleic acid fragment, wherein the SNP site is identified by using an extension primer, a 3'-end of the extension primer is extended by a single nucleotide which is complementary to a base of the SNP site, and thus an extended extension primer is obtained; (S40) performing a purification reaction to purify the extended extension primer; and (S50) measuring a molecular weight of the extended extension primer, and determining a type of a base of the single nucleotide based upon the molecular weight, thereby determining whether deletion occurs to the SNP site.

Now refer to the following non-limiting embodiments for further understanding the present disclosure. It should be appreciated that the following embodiments are merely exemplary, and should not be regarded as limitations for the present disclosure.

Designs of polymerase chain reaction (PCR), amplification primers and extension primers:

In step (S10) of the method of the present disclosure, a polymerase chain reaction (PCR) is performed on a specimen, wherein a nucleic acid fragment containing a SNP site in the specimen is amplified by using a pair of amplification primers to obtain an amplified nucleic acid fragment.

In general, DNA extraction is performed on the specimen prior to the PCR. For example, DNA is extracted by using a commercially available DNA extraction kit, such as the QIAGEN Blood Mini Kit®. A lysis buffer is used to dissolve the cells sampled from the patient's endothelium to free DNA from the cells. Next, under certain conditions, the DNA is passed through a column provided by the extraction kit, combines with a silica-gel membrane in the column, and remains on the membrane. Alcohol and the washing buffer are used to wash the membrane, and remove the impurities after centrifugation. Finally the DNA is eluted with pure water to extract the DNA. For detailed extraction procedures, refer to the instruction manual of the DNA extraction kit. The above DNA extraction method is an exemplary embodiment, and various DNA extraction methods can be used in the method for detecting the SNP site of the present disclosure, and therefore the scope of the present application should not be limited thereto.

A pair of amplification primers is designed in accordance with the above SNP site, and the sequences of the pair of amplification primers are respectively at least partially complementary to the sequences of the 5' ends and the 3' ends of the nucleic acid fragment containing the SNP site. For example, the nucleic acid fragment containing the SNP site is approximately 100 nucleotides in size. Preferably, the sequences of the pair of amplification primers are fully respectively complementary to the sequences of the 5' ends and the 3' ends of the nucleic acid fragment containing the SNP site. Since the sequences of the pair of amplification primers are complementary to the nucleic acid fragment containing the SNP site, the pair of amplification primers respectively recognize and bind to the 5' end and the 3' end of the nucleic acid fragment in the PCR, and the nucleic acid fragment between the pair of amplification primers is amplified. The principle of the polymerase chain reaction (PCR) should be understood by those skilled in the art and will not redundantly be described in this specification.

As to the design of the amplification primers and the extension primers, for example, a pair of amplification primers, which are respectively complementary to the 5' end and the 3' end of the nucleic acid fragment containing the SNP site, are about 15 nucleotides in length, or more nucleotides, or fewer nucleotides. The extension primers used in the extension reaction of step (S30) are about 15-23 nucleotides in length, or more nucleotides, or fewer nucleotides. However, in order to avoid that the sizes of the amplification primers and the sizes of the extension primers are too close to each other, so that the signals of the amplification primers appear in the mass spectrometer spectrum to cause interference when the extended extension primers are being detected by the mass spectrometer, a TAG nucleic acid fragment of 10 nucleotides is added to the 5' end of the amplification primers to increase the molecular weight differences between the amplification primers and the extension primers. For example, in general, the mass spectrometer is used to detect the signals of the extended extension primers having molecular weights between 4000 Da and 9000 Da, and the molecular weights of the amplification primers attached with the TAG nucleic acid fragment at the 5' end are much greater than 9000 Da. Thus, the signals of the amplification primers do not appear in the mass spectrometer spectrum observing the extended extension primers. In an embodiment of the present disclosure, the TAG nucleic acid fragment is, for example, SEQ ID NO: 19 (ACGTTGGATG). However, other TAG nucleic acid fragments may also be used, and are generally not complementary to the nucleic acid fragment containing the SNP site. However, the lengths and the molecular weights of the amplification primers described above are only examples. The method for detecting the SNP site of the present disclosure is applicable to amplification primers having various lengths. Therefore, the scope of the present disclosure should not be limited thereto.

In an embodiment of the present disclosure, the reaction concentration conditions of the PCR for amplifying the nucleic acid fragment are as follows: the reaction solution of 5 t l contains approximately the specimen DNA of 40 ng/μl, Taq polymerase of 8 units, the pair of amplification primers of 500 nmol, $MgCl_2$ of 2 mM, 1×PCR buffer, and dNTP of 50 mM (provided by the PCR accessory and Enzyme kit purchased from Agena Company). Reaction temperature conditions are as follows: Denaturation is performed at 95° C. for 2 minutes. Afterwards, denaturation at 95° C. for 30 seconds, annealing at 56° C. for 30 seconds, and elongation at 72° C. for 1 minute are repeated for 45 cycles. The above polymerase chain reaction is only an example, and various polymerase chain reactions can be utilized in the method for detecting the SNP site of the present disclosure. Therefore, the scope of the present application should not be limited thereto.

In step (S10) of the method, the target fragment is amplified by the PCR. The conditions of the amplification reaction are well known to those skilled in the art. The exemplary reaction conditions are also described above in detail in the embodiments of the present disclosure. Moreover, based upon the specific sequences of the primers of the present disclosure, it is within the ability of those skilled in the art to make certain changes or optimization for the conditions of the amplification reaction.

Refer to Table I as follows. In a preferred embodiment of the present disclosure, when the SNP site to be detected is the SNP site on exon 7, SEQ ID NO: 1 and SEQ ID NO: 2 are used as the pair of amplification primers in the amplification reaction, and SEQ ID NO: 3 is used as the extension primer in the extension reaction of subsequent step (S30). In another preferred embodiment of the present disclosure, when the SNP site to be detected is the first SNP site on the intron 7, SEQ ID NO: 4 and SEQ ID NO: 5 are used as the pair of amplification primers in the amplification reaction, and SEQ ID NO: 6 is used as the extension primer in the extension reaction of subsequent step (S30).

In a preferred embodiment of the present disclosure, when a plurality of SNP sites are to be detected, the plurality of pairs of amplification primers corresponding to the SNP sites are used in the amplification reaction, and the plurality of extension primers corresponding to the SNP sites are used in the extension reaction of subsequent step (S30). For example, the plurality of amplification primers are mixed into one reaction tube, and the plurality of extension primers are mixed into another reaction tube. All of the primers disclosed in Table I of the present disclosure are effortfully and repeatedly modified and improved so as to ensure that all of the primers do not interact with each other and interfere with each other. Therefore, the plurality of SNP sites can simultaneously be detected, thereby improving the efficiency and saving costs. In addition, the detection of the plurality of SNP sites can be performed by sampling only 2 μl of the specimens, thereby increasing detection convenience, success rate, and precision. For example, when it is desired to simultaneously detect the SNP site on exon 7 and the first SNP site on intron 7, the pair of SEQ ID NO: 1 and SEQ ID NO:2 and the pair of SEQ ID NO:4 and SEQ ID NO:5 are simultaneously used as the pairs of amplification primers in the amplification reaction, and SEQ ID NO: 3 and SEQ ID NO: 6 are used as the extension primers in the extension reaction of subsequent step (S30).

In a most preferred embodiment of the present disclosure, all of the SNP sites listed in Table I below are simultaneously be detected, all amplification primers listed in Table I below are used in the amplification reaction, and all of the extension primers listed in Table I below are used in the extension reaction of subsequent step (S30). For example, all of the amplification primers listed in Table I are mixed into one reaction tube, and all of the extension primers listed in Table I are mixed into another reaction tube. All of the primers disclosed in Table I of the present disclosure are effortfully and repeatedly modified and improved so as to ensure that all of the primers do not interact with each other and interfere with each other. Therefore, all of the SNP sites can simultaneously be detected, thereby improving the efficiency and saving costs. In addition, the detection of the plurality of SNP sites can be performed by sampling only 2 t 1 of the specimens, thereby increasing detection convenience, success rate, and precision.

TABLE I

| Sequence Number | Primer Sequence | Target SNP Site | Primer Type |
|---|---|---|---|
| SEQ ID NO: 1 | GAATGTGAGCACCTT CCTTC | Exon 7 | First Amplification Primer |
| SEQ ID NO: 2 | AACATCCATATAAAG CTATC | Exon 7 | Second Amplification Primer |
| SEQ ID NO: 3 | TTTATTTTCCTTACA GGGTTT | Exon 7 | Extension Primer |
| SEQ ID NO: 4 | GCTCTTTATTGTGAA AGTATG | Intron 7-1 | First Amplification Primer |

TABLE I-continued

| Sequence Number | Primer Sequence | Target SNP Site | Primer Type |
|---|---|---|---|
| SEQ ID NO: 5 | GGTTTGTGGAAAAC AAATG | Intron 7-1 | Second Amplification Primer |
| SEQ ID NO: 6 | ACATTTAAAAAGTTC AGATGTTA | Intron 7-1 | Extension Primer |
| SEQ ID NO: 7 | GCTCTTTATTGTGAA AGTATG | Intron 7-2 | First Amplification Primer |
| SEQ ID NO: 8 | GGTTTGTGGAAAAC AAATG | Intron 7-2 | Second Amplification Primer |
| SEQ ID NO: 9 | TTCTCATACTTAACT GGTTGGTT | Intron 7-2 | Extension Primer |
| SEQ ID NO: 10 | GGAATGGGTAACTCT TCTTG | Exon 8 | First Amplification Primer |
| SEQ ID NO: 11 | TTTCTCAACTGCCTC ACCAC | Exon 8 | Second Amplification Primer |
| SEQ ID NO: 12 | CCTCCCACCCCCACC | Exon 8 | Extension Primer |
| SEQ ID NO: 13 | GCCCACCTTGGTCTC CTAAA | Control | First Amplification Primer |
| SEQ ID NO: 14 | ACCTTTGAGACACTT GCC | Control | Second Amplification Primer |
| SEQ ID NO: 15 | TGTCATCTCTTGTGG G | Control | Extension Primer |
| SEQ ID NO: 16 | GCATGCCTAATATTT TCAGGG | Control (Sex Chromosome) | First Amplification Primer |
| SEQ ID NO: 17 | ACCCCTTTGAAGTGG TAC | Control (Sex Chromosome) | Second Amplification Primer |
| SEQ ID NO: 18 | AGTGGTACCAGAGC AT | Control (Sex Chromosome) | Extension Primer |
| SEQ ID NO: 19 | ACGTTGGATG | | TAG sequence |

Dephosphorylation (SAP Enzyme Treatment):

In step (S20) of the present disclosure, a dephosphorylation reaction is performed on the amplified nucleic acid fragment to remove a phosphate at a 5' end of the amplified nucleic acid fragment in the PCR. For example, by using 0.3 U of shrimp alkaline phosphatase (SAP) and 1×SAP buffer, a phosphate at a 5' end of the dNTPs in the product of the PCR and a phosphate at a 5' end of the amplified nucleic acid fragment are removed, so as to dephosphorylate the unreacted dNTPs, thereby preventing dNTPs from participating in subsequent reactions and ensuring that only a single nucleotide is added during the extension reaction. The above dephosphorylation reaction is an exemplary embodiment, and various dephosphorylation reactions can be utilized in the method for detecting the SNP site of the present disclosure. Therefore, the scope of the present application should not be limited thereto.

Extension Reaction:

In step (S30) of the present disclosure, an extension reaction is performed on the amplified nucleic acid fragment, wherein the SNP site is identified by using an extension primer, a 3'-end of the extension primer is extended by a single nucleotide which is complementary to a base of the SNP site, and thus an extended extension primer is obtained.

For example, the extension primers used in the extension reaction of step (S30) are about 15-23 nucleotides in length, or more nucleotides, or fewer nucleotides. The sequence of the extension primer is complementary to the sequence preceding the SNP site (i.e., the sequence preceding the 5' end of the SNP site), and thus binds directly to the sequence in front of the SNP site to identify the SNP site. Under an appropriate polymerase action and reaction conditions, the 3' end of the extension primer is extended by a single nucleotide which is complementary to the base of the SNP site, resulting in an extended extension primer. Therefore, the difference between the resultant extended extension primer (i.e., product) and the original extension primer is only that a single nucleotide is added to the 3' end of the resultant extended extension primer. For example, the base of the single nucleotide includes four types, including an adenine (A), a thymine (T), a cytosine (C), and a guanine (G). When the base of the SNP site is a thymine (T), the based of the added single nucleotide is an adenine (A). When the base of the SNP site is an adenine (A), the based of the added single nucleotide is a thymine (T). When the base of the SNP site is a cytosine (C), the based of the added single nucleotide is a guanine (G). When the base of the SNP site is a guanine (G), the based of the added single nucleotide is cytosine (C).

Because the added single nucleotide may have different bases, the extended extension primer may have different molecular weights. In the subsequent step (S50), the molecular weight of the extended extension primer is detected by a mass spectrometer. Based upon the molecular weight, the base of the added single nucleotide is determined, and whether deletion occurs to the SNP site is determined.

In an exemplary embodiment of the disclosure, the nucleotides used in the extension reaction are modified ddNTPs for ensuring that the extension reaction extends only a single nucleotide (since nucleotides cannot be added to the 3' end of the ddNTPs lacking an oxygen), and increasing the molecular weight difference between the extended extension primers, thereby improving the resolution of the mass spectrometry detection in step (S50). The molecular weights of the four ddNTPs are as follows: ddATP is 271.2 Da, ddTTP is 327.1 Da, ddCTP is 247.2 Da, and ddGTP is 287.2 Da, where the molecular weight differences are above 16 Da.

In an exemplary embodiment of the present disclosure, the polymerase used in the extension reaction is iPLEX enzyme (purchased from Agena Corporation, USA). The appropriate condition and procedures are as follows: The iPLEX enzyme polymerase and the extension primer are added into the terminator mix buffer solution. Denaturation is first performed at 95° C. for 30 seconds. Afterwards, denaturation at 95° C. for 5 seconds and 4 small cycles of (annealing at 56° C. for 30 seconds and elongation at 80° C. for 5 seconds) are repeated for 40 cycles. Finally, elongation is performed at 72° C. for 3 minutes. The above extension reaction is an exemplary embodiment, and various extension reactions can be utilized in the method for detecting the SNP site of the present disclosure, and therefore the scope of the present application should not be limited thereto.

In step (S30) of the method, the extension reaction is performed on the target fragment, and the conditions for the extension reaction are similar to those for a general polymerase chain reaction (PCR), are well known to those skilled in the art. The exemplary reaction conditions are also described above in detail in the embodiments of the present disclosure. Moreover, based upon the specific sequences of the primers of the present disclosure, it is within the ability of those skilled in the art to make certain changes or optimization for the conditions of the amplification reaction.

In a preferred embodiment of the present disclosure, as described above and shown in Table I above, when the SNP site to be detected is the SNP site on exon 7, SEQ ID NO: 1 and SEQ ID NO: 2 are used as the pair of amplification primers in the amplification reaction of previous step (S10), and SEQ ID NO: 3 is used as the extension primer in the extension reaction of present step (S30).

In a preferred embodiment of the present disclosure, when a plurality of SNP sites are to be detected, the plurality of pairs of amplification primers corresponding to the SNP sites are used in the amplification reaction in previous step (S10), and the plurality of extension primers corresponding to the SNP sites are used in the extension reaction of present step (S30). For example, the plurality of amplification primers are mixed into one reaction tube, and the plurality of extension primers are mixed into another reaction tube. All of the primers disclosed in Table I of the present disclosure are effortfully and repeatedly modified and improved so as to ensure that all of the primers do not interact with each other and interfere with each other. All of the amplification primers listed in Table I above can even be used in the amplification reaction of previous step (S10), and all of the extension primers listed in Table I above can even be used in the extension reaction of present step (S30). Therefore, all of the SNP sites can simultaneously be detected, thereby improving the efficiency and saving costs. In addition, the detection of the plurality of SNP sites can be performed by sampling only 2 μl of the specimens, thereby increasing detection convenience, success rate, and precision.

Purification Reaction:

In step (S40), a purification reaction is performed to purify the extended extension primer. For example, after adding 6 mg of resin (available from Agena Company, USA) to remove the salt ions in the extension reaction product for undergoing the reaction for 20 minutes, the resin is fully combined with cations in the reaction system, thereby removing salts from the reaction system. Then, after centrifuged at 4000 rpm for five minutes, the resin is precipitated, and the supernatant is taken. The above purification reaction is an exemplary embodiment, and various purification reactions can be used in the method for detecting the SNP site of the present disclosure. Therefore, the scope of the present application should not be limited thereto.

Measurement of the Size of the Nucleic Acid Fragments:

In step (S50), a molecular weight of the extended extension primer is measured by using a mass spectrometer, and determining a type of a base of the single nucleotide based upon the molecular weight, thereby determining the genotype of the SNP site. For example, about 7 nl of the purified product is dispensed on the chips (SpectroCHIP®, America Sequenom Inc.) containing the substrate, and the nucleic acid fragments are excited to fly in the vacuum electric field by using the mass spectrometer (MassARRAY analyzer 4 (Agena)). The molecular weight of each nucleic acid fragment is obtained by the sensor capturing the signal of each nucleic acid cleavage fragment. Based upon the molecular weight, the type of the base of the added single nucleotide is determined. The mass spectrometry data is analyzed using TYPER 4.0 (Agena) software. The above method utilizes a mass spectrometer to detect molecular weights of nucleic acid fragments without using the conventional sequencing method of gel electrophoresis. Since different molecules have different molecular weights, only one single nucleotide difference between two different nucleic acid fragments can be accurately detected. Therefore, stability and accuracy of identification of nucleic acid fragments are greatly improved.

However, in step (S50), the method of determining the type of the base of the added single nucleotide should not be limited to the use of a mass spectrometer. Another alternative embodiment provided herein is the use of a fluorescent electrophoresis. That is, four types of nucleotides (A, T, C, and G) respectively labeled with fluorescent markers of four different colors are used in the extension reaction in step (S30). In step (S50), the sizes of the nucleic acid fragments are identified by using gel electrophoresis, which, at most, is able to distinguish nucleic acid fragments with a single nucleotide size difference. Then, based upon the colors of the fluorescent markers (e.g., the fluorescence type) labeled to the extended extension primer, the type of the base of the added single nucleotide is determined. Therefore, the fluorescent electrophoresis can be used as an alternative solution to the mass spectrometry. However, in the following, the mass spectrometry is used to determine the type of the base of the added single nucleotide as an exemplary embodiment of the present disclosure, but the scope of the present application should not be limited to the use of a mass spectrometer. Any method which is able to determine the type of the base of the added single nucleotide should apply.

Figure 3A:
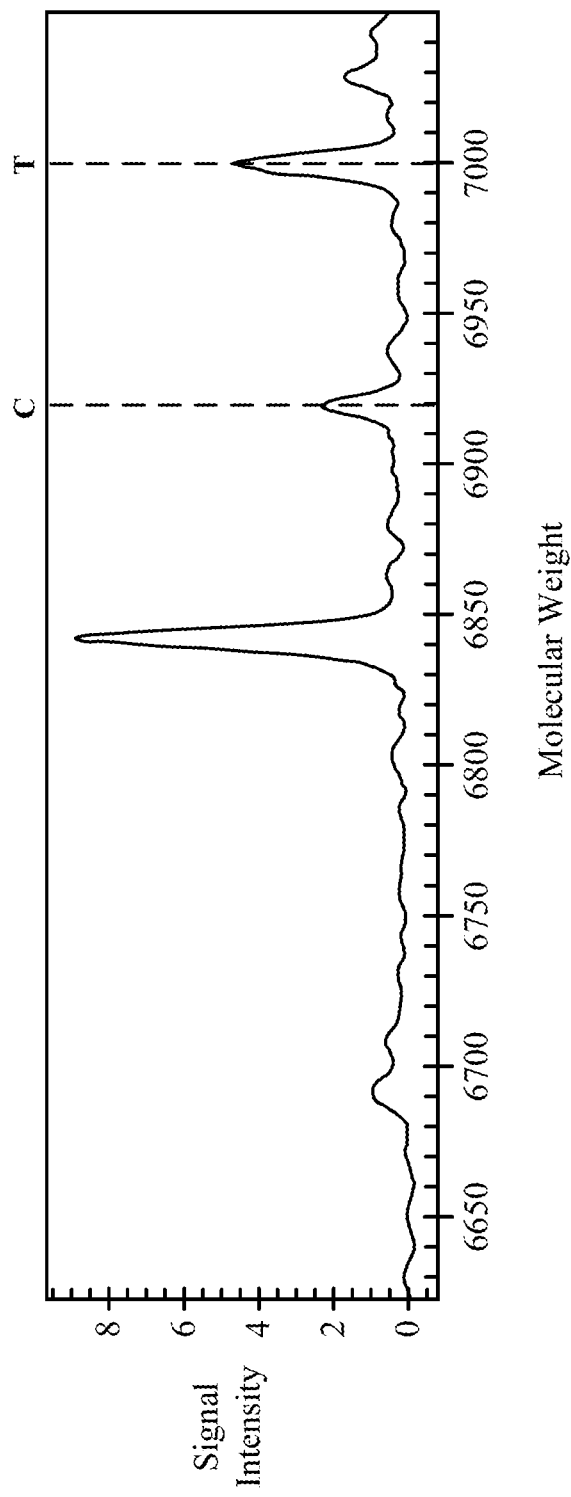

The detection results of the present disclosure are shown in FIG. 3A to FIG. 4B, where the horizontal axis indicates the molecular weight and the vertical axis indicates the signal intensity. FIG. 3A to FIG. 3C show detection of a SNP site on exon 7 of the SMA genes from a negative control group and to-be-tested specimens, by using the extension primer SEQ ID NO: 3 according to an embodiment of the present disclosure, wherein FIG. 3A shows the spectrum from the negative control group, and FIG. 3B and FIG. 3C show the spectrums from the to-be-tested specimens. In the spectrum of the mass spectrometer of FIG. 3A, the signals of two extension products of the extension primer, SEQ ID NO: 3, are detected, which respectively are a fragment with a molecular weight of 6,920 Da and a fragment with a molecular weight of 7,000 Da, and respectively correspond to the cytosine (C) at the SNP site on exon 7 of the SMN1 gene and the thymidine (T) at the SNP site on exon 7 of the SMN2 gene, thereby indicating that deletion occurs to neither the SNP site on exon 7 of the SMN1 gene nor the SNP site on exon 7 of the SMN2 gene in the negative control group.

Figure 3B:
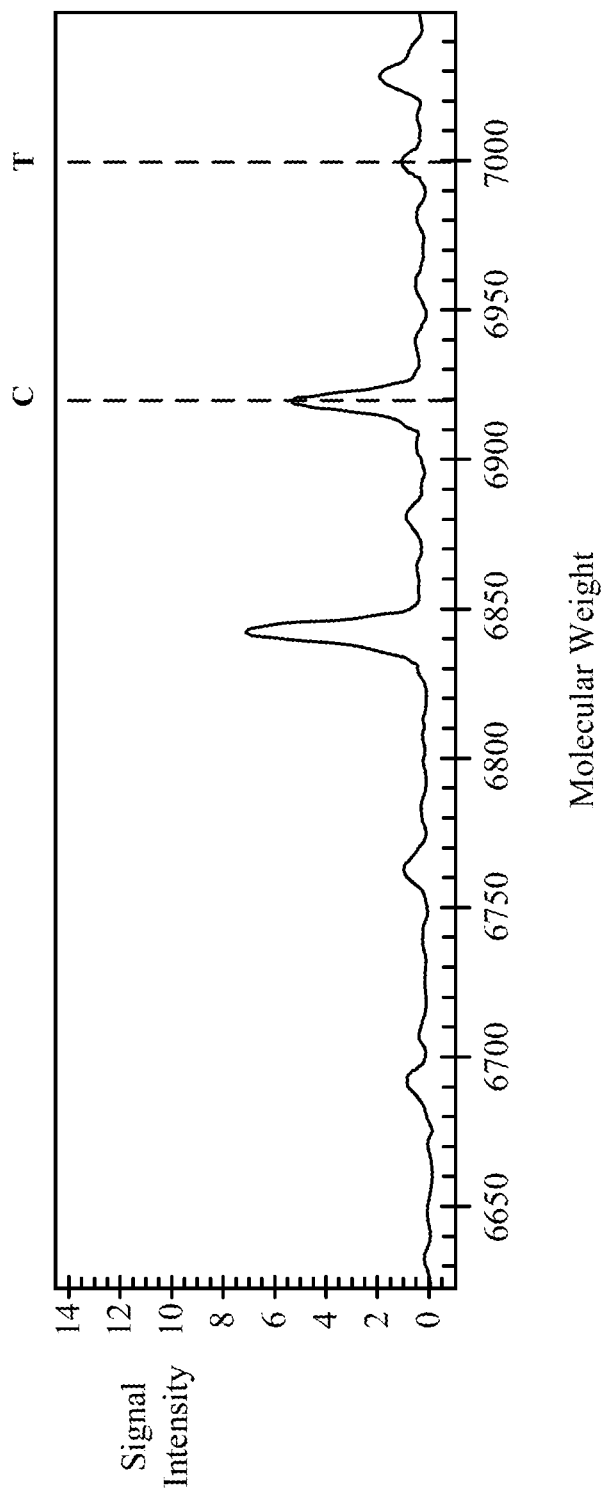
Figure 3C:
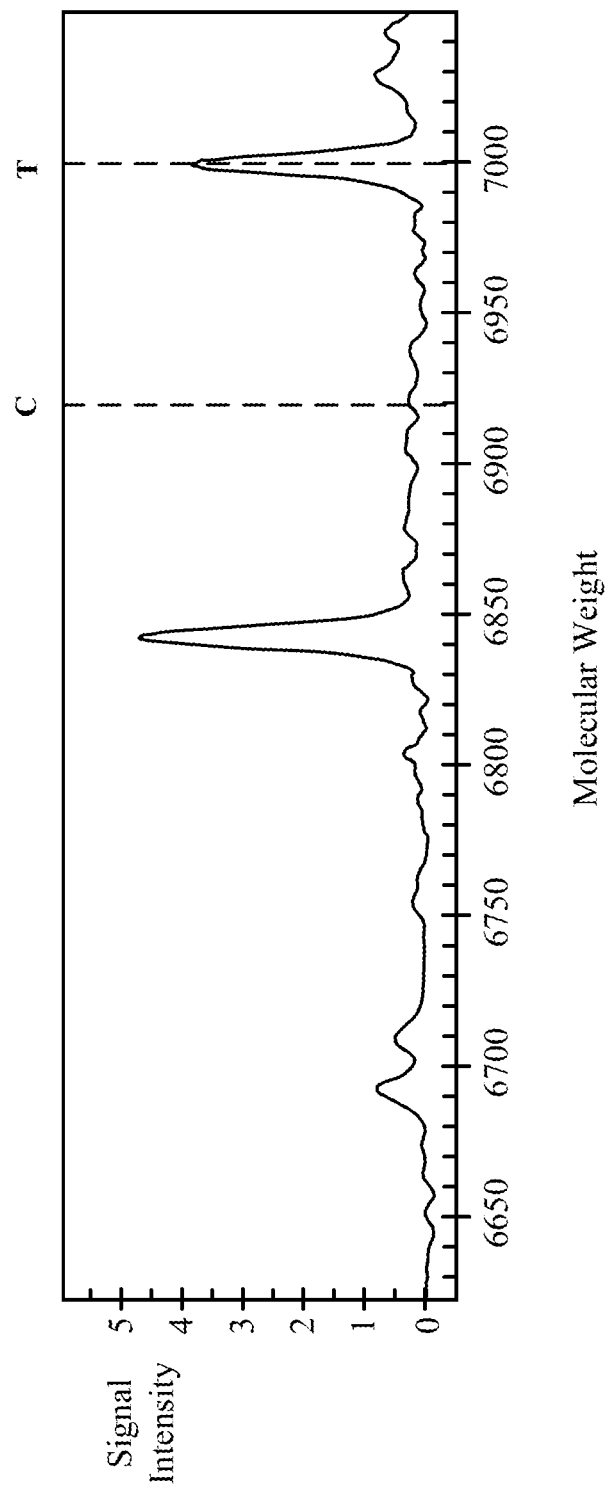

In the spectrum of the mass spectrometer of FIG. 3B, only the signal of one extension product of the extension primer, SEQ ID NO: 3, is detected, which is a fragment with a molecular weight of 6,920 Da, and corresponds to the cytosine (C) at the SNP site on exon 7 of the SMN1 gene, thereby indicating that deletion does not occur to the SNP site on exon 7 of the SMN1 gene in the to-be-tested specimen, but occurs to the SNP site on exon 7 of the SMN2 gene in the to-be-tested specimen. However, as described above, about 85% of the protein expressed by the SMN2 gene is a truncated unstable SMN protein. The protein expressed by the SMN2 gene does not have a biological significance. When the SMN2 gene is defective, it basically does not cause disorder. Therefore, in FIG. 3B, the subject from whom the to-be-tested specimen derives has a low risk of suffering from spinal muscular atrophy. In the spectrum of the mass spectrometer of FIG. 3C, only the signal of one extension products of the extension primer, SEQ ID NO: 3, is detected, which is a fragment with a molecular weight of 7,000 Da, and corresponds to the thymidine (T) at the SNP site on exon 7 of the SMN2 gene, thereby indicating that deletion does not occur to the SNP site on exon 7 of the SMN2 gene in the to-be-tested specimen, but occurs to the SNP site on exon 7 of the SMN1 gene in the to-be-tested specimen. As described above, the protein expressed by the SMN1 gene is a full-length stable SMN protein, and has a biological significance. Therefore, in FIG. 3C, the subject from whom the to-be-tested specimen derives has a high risk of suffering from spinal muscular atrophy.

Figure 4A:
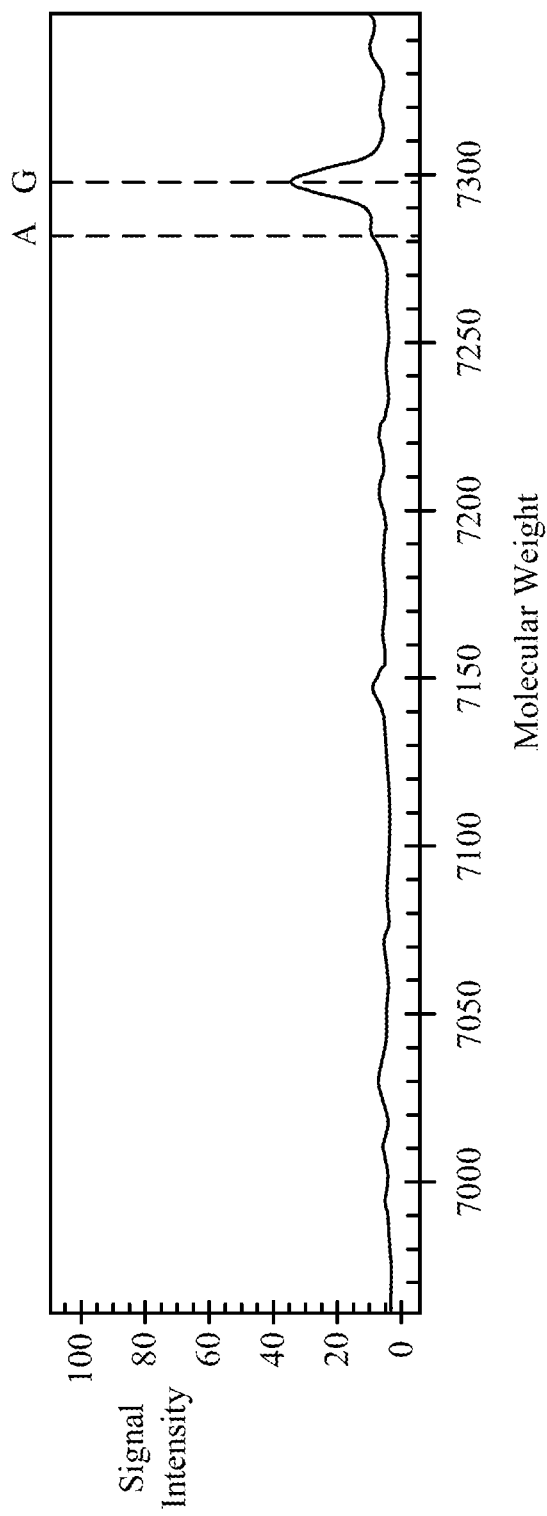
Figure 4B:
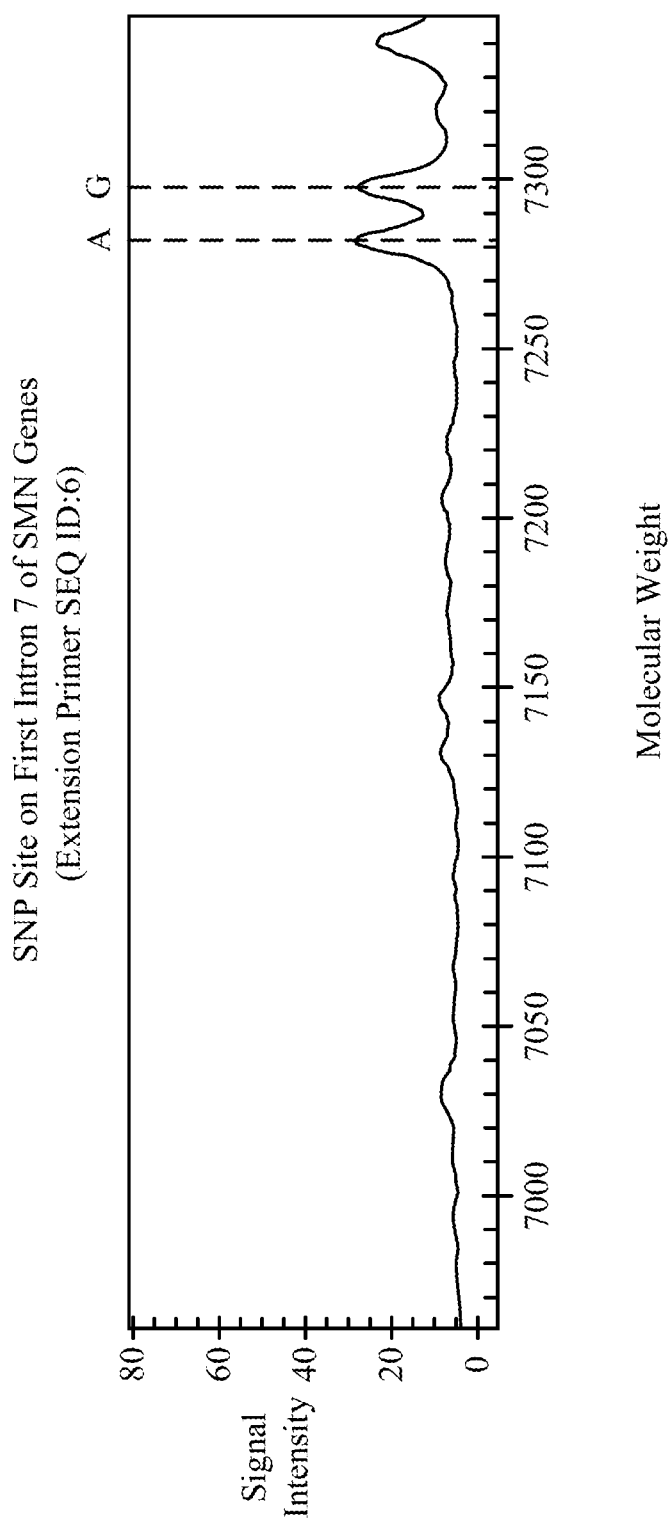

FIG. 4A to FIG. 4B show detection of the first SNP site on intron 7 of the SMA genes from a positive control group and a to-be-tested specimen, by using the extension primer SEQ ID NO: 6 according to an embodiment of the present disclosure, wherein FIG. 4A shows the spectrum from the positive control group, and FIG. 4B shows the spectrum from the to-be-tested specimens. In the spectrum of the mass spectrometer of FIG. 4A, only the signal of one extension product of the extension primer, SEQ ID NO: 6, is detected, which is a fragment with a molecular weight of 7,298 Da, and corresponds to the guanine (G) at the first SNP site on intron 7 of the SMN2 gene, thereby indicating that deletion does not occur to the first SNP site on intron 7 of the SMN2 gene in the to-be-tested specimen, but occurs to the first SNP site on intron 7 of the SMN1 gene in the to-be-tested specimen. As described above, the protein expressed by the SMN1 gene is a full-length stable SMN protein, and has a biological significance. Therefore, the subject from whom the positive control group derives has a high risk of suffering from spinal muscular atrophy. In the spectrum of the mass spectrometer of FIG. 4B, the signals of two extension products of the extension primer, SEQ ID NO: 6, are detected, which respectively are a fragment with a molecular weight of 7,282 Da and a fragment with a molecular weight of 7,298 Da, and respectively correspond to the adenine (A) at the first SNP site on intron 7 of the SMN1 gene and the guanine (G) at the first SNP site on intron 7 of the SMN2 gene, thereby indicating that deletion does not occur to the first SNP site on intron 7 of the SMN1 gene and the SMN2 gene in the to-be-tested specimen. The subject from whom the to-be-tested specimen derives has a low risk of suffering from spinal muscular atrophy.

However, the above-described experimental results are merely representative of the practical application of the method for detecting the SNP sites on the SMA genes of the present disclosure. Therefore, the scope of the present application should not be limited to the experimental results.

In the method for detecting the plurality of SNP sites of the SMA genes of the present disclosure, deletion occurring to any one of the four SNP sites on the SMN1 gene represents the deletion occurring to the SMN1 gene. However, in general, the deletion on the SMN1 gene often occurs to exon 7, intron 7, and exon 8, and is usually a wide range of deletion. Hence, when the deletion occurs to any one of the four SNP sites, the deletion usually occurs to the other three SNP sites as well. Only the protein expressed by the SMN1 gene has biological significance, but the protein expressed by the SMN2 gene does not. Therefore, if the deletion occurs to all of the four SNP sites on the SMN1 gene, the to-be-tested specimen is determined to be derived from a patient with spinal muscular atrophy.

However, the bio-molecular genetic characteristics described above merely show the genetically significance of the method for detecting the plurality of SNP sites of the SMA genes of the present disclosure Therefore, the scope of the present application should not be limited to the bio-molecular genetic characteristics.

An object of the present disclosure is to provide a method for identifying homozygous deletion on a survival motor neuron 1 (SMN1) gene. The method of the present disclosure (1) simultaneously detect a plurality of single nucleotide polymorphism (SNP) sites in the same reaction, greatly reducing the analysis cost; (2) is simple and rapid, and is applicable to various specimens, such as fresh tissue, frozen tissue, formalin-fixed paraffin-embedded (FFPE) tissue, genomic DNA extracted from cell lines, or plasma circulating cell-free DNA, etc. (3) Since the SNP sites (loci) are located in the region of the SMN1 gene where deletion occurs with high possibility, the deletion on the SMN1 gene can be confirmed by detecting the SNP sites, the deletions in different sizes in tiny amounts of specimens can also be accurately detected, and the method of the present disclosure is greatly efficient. (4) Since the deletion on the SMN1 gene is highly correlated with spinal muscular atrophy (SMA), quickly identifying the genotypes of the SMA genes of the patients by the method of the present disclosure is valuable for the study of spinal muscular atrophy.

The present disclosure has been described with a preferred embodiment thereof and it is understood that various modifications, without departing from the spirit of the present disclosure, are in accordance with the embodiments of the present disclosure. Hence, the embodiments described are intended to cover the modifications within the scope and the spirit of the present disclosure, rather than to limit the present disclosure.

What is claimed is:

1. A method for detecting a single nucleotide polymorphism (SNP) site on spinal muscular atrophy (SMA) genes including a SMN1 gene or a SMN2 gene, comprising steps of:

(S10) performing a polymerase chain reaction (PCR) on a specimen, wherein a nucleic acid fragment containing a SNP site in the specimen is amplified by using a pair of amplification primers to obtain an amplified nucleic acid fragment;

(S20) performing a dephosphorylation reaction on the amplified nucleic acid fragment to remove a phosphate at a 5' end of the nucleic acid fragment in the PCR;

(S30) performing an extension reaction on the amplified nucleic acid fragment, wherein the SNP site is identified by using an extension primer, a 3'-end of the extension primer is extended by a single nucleotide which is complementary to a base of the SNP site, and thus an extended extension primer is obtained;

(S40) performing a purification reaction to purify the extended extension primer; and (S50) measuring a molecular weight of the extended extension primer, and obtaining at least a type of a base of the single nucleotide based upon the molecular weight, wherein when two types of the bases are detected, then none of the SMN1 gene or the SMN2 gene at the SNP site has a deletion; and when only one type of the base is detected, then one of the SMN1 gene or the SMN2 gene at the SNP site has a deletion;

wherein the pair of amplification primers is
a first amplification primer pair, wherein a forward primer of the first amplification primer pair consists of the DNA sequence of ACGTTGGATGGCTCTT-TATTGTGAAAGTATG (SEQ ID NO: 22), and a backward primer of the first amplification primer pair consists of the DNA sequence of ACGTTG-GATGGGTTTGTGGAAAACAAATG (SEQ ID NO: 23);

wherein the extension primer is
a first extension primer consisting of the DNA sequence of ACATTTAAAAAGTTCAGATGTTA (SEQ ID NO: 6).

* * * * *

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: amplification primer

<400> SEQUENCE: 1
gaatgtgagc accttccttc                                           20

<210> SEQ ID NO 2
<211> LENGTH: 20
<212> TYPE: DNA
<213> ORGANISM: Artificial Sequence
<220> FEATURE:
<223> OTHER INFORMATION: amplification primer

<400> SEQUENCE: 2
aacatccata taaagctatc                                           20

<210> SEQ ID NO 3
<211> LENGTH: 21
<212> TYPE: DNA
<213> ORGANISM: Artificial Sequence
<220> FEATURE:
<223> OTHER INFORMATION: extension primer

<400> SEQUENCE: 3
tttattttcc ttacagggtt t                                         21

<210> SEQ ID NO 4
<211> LENGTH: 21
<212> TYPE: DNA
<213> ORGANISM: Artificial Sequence
<220> FEATURE:
<223> OTHER INFORMATION: amplification primer

<400> SEQUENCE: 4
gctctttatt gtgaaagtat g                                         21

<210> SEQ ID NO 5
<211> LENGTH: 19
<212> TYPE: DNA
<213> ORGANISM: Artificial Sequence
<220> FEATURE:
<223> OTHER INFORMATION: amplification primer

<400> SEQUENCE: 5
ggtttgtgga aaacaaatg                                            19

<210> SEQ ID NO 6
<211> LENGTH: 23
<212> TYPE: DNA
<213> ORGANISM: Artificial Sequence
<220> FEATURE:
<223> OTHER INFORMATION: extension primer

<400> SEQUENCE: 6
acatttaaaa agttcagatg tta                                       23

<210> SEQ ID NO 7
<211> LENGTH: 21
<212> TYPE: DNA
<213> ORGANISM: Artificial Sequence

```
<220> FEATURE:
<223> OTHER INFORMATION: amplification primer

<400> SEQUENCE: 7
gctctttatt gtgaaagtat g                                          21

<210> SEQ ID NO 8
<211> LENGTH: 19
<212> TYPE: DNA
<213> ORGANISM: Artificial Sequence
<220> FEATURE:
<223> OTHER INFORMATION: amplification primer

<400> SEQUENCE: 8
ggtttgtgga aacaaatg                                              19

<210> SEQ ID NO 9
<211> LENGTH: 23
<212> TYPE: DNA
<213> ORGANISM: Artificial Sequence
<220> FEATURE:
<223> OTHER INFORMATION: extension primer

<400> SEQUENCE: 9
ttctcatact taactggttg gtt                                        23

<210> SEQ ID NO 10
<211> LENGTH: 20
<212> TYPE: DNA
<213> ORGANISM: Artificial Sequence
<220> FEATURE:
<223> OTHER INFORMATION: amplification primer

<400> SEQUENCE: 10
ggaatgggta actcttcttg                                            20

<210> SEQ ID NO 11
<211> LENGTH: 20
<212> TYPE: DNA
<213> ORGANISM: Artificial Sequence
<220> FEATURE:
<223> OTHER INFORMATION: amplification primer

<400> SEQUENCE: 11
tttctcaact gcctcaccac                                            20

<210> SEQ ID NO 12
<211> LENGTH: 15
<212> TYPE: DNA
<213> ORGANISM: Artificial Sequence
<220> FEATURE:
<223> OTHER INFORMATION: extension primer

<400> SEQUENCE: 12
cctcccaccc ccacc                                                 15

<210> SEQ ID NO 13
<211> LENGTH: 20
<212> TYPE: DNA
<213> ORGANISM: Artificial Sequence
<220> FEATURE:
<223> OTHER INFORMATION: amplification primer

<400> SEQUENCE: 13
gcccaccttg gtctcctaaa                                            20
```

```
<210> SEQ ID NO 14
<211> LENGTH: 18
<212> TYPE: DNA
<213> ORGANISM: Artificial Sequence
<220> FEATURE:
<223> OTHER INFORMATION: amplification primer

<400> SEQUENCE: 14
acctttgaga cacttgcc                                                 18

<210> SEQ ID NO 15
<211> LENGTH: 16
<212> TYPE: DNA
<213> ORGANISM: Artificial Sequence
<220> FEATURE:
<223> OTHER INFORMATION: extension primer

<400> SEQUENCE: 15
tgtcatctct tgtggg                                                   16

<210> SEQ ID NO 16
<211> LENGTH: 21
<212> TYPE: DNA
<213> ORGANISM: Artificial Sequence
<220> FEATURE:
<223> OTHER INFORMATION: amplification primer

<400> SEQUENCE: 16
gcatgcctaa tattttcagg g                                             21

<210> SEQ ID NO 17
<211> LENGTH: 18
<212> TYPE: DNA
<213> ORGANISM: Artificial Sequence
<220> FEATURE:
<223> OTHER INFORMATION: amplification primer

<400> SEQUENCE: 17
acccctttga agtggtac                                                 18

<210> SEQ ID NO 18
<211> LENGTH: 16
<212> TYPE: DNA
<213> ORGANISM: Artificial Sequence
<220> FEATURE:
<223> OTHER INFORMATION: extension primer

<400> SEQUENCE: 18
agtggtacca gagcat                                                   16

<210> SEQ ID NO 19
<211> LENGTH: 10
<212> TYPE: DNA
<213> ORGANISM: Artificial Sequence
<220> FEATURE:
<223> OTHER INFORMATION: TAG Sequence

<400> SEQUENCE: 19
acgttggatg                                                          10

<210> SEQ ID NO 20
<211> LENGTH: 30
<212> TYPE: DNA
<213> ORGANISM: Artificial Sequence
<220> FEATURE:
<223> OTHER INFORMATION: TAG Sequence in combination with Extension
```

```
                    Primer

<400> SEQUENCE: 20
acgttggatg gaatgtgagc accttccttc                                          30

<210> SEQ ID NO 21
<211> LENGTH: 30
<212> TYPE: DNA
<213> ORGANISM: Artificial Sequence
<220> FEATURE:
<223> OTHER INFORMATION: TAG Sequence in combination with Extension
      Primer

<400> SEQUENCE: 21
acgttggatg aacatccata taaagctatc                                          30

<210> SEQ ID NO 22
<211> LENGTH: 31
<212> TYPE: DNA
<213> ORGANISM: Artificial Sequence
<220> FEATURE:
<223> OTHER INFORMATION: TAG Sequence in combination with Extension
      Primer

<400> SEQUENCE: 22
acgttggatg gctctttatt gtgaaagtat g                                        31

<210> SEQ ID NO 23
<211> LENGTH: 29
<212> TYPE: DNA
<213> ORGANISM: Artificial Sequence
<220> FEATURE:
<223> OTHER INFORMATION: TAG Sequence in combination with Extension
      Primer

<400> SEQUENCE: 23
acgttggatg ggtttgtgga aaacaaatg                                           29

<210> SEQ ID NO 24
<211> LENGTH: 31
<212> TYPE: DNA
<213> ORGANISM: Artificial Sequence
<220> FEATURE:
<223> OTHER INFORMATION: TAG Sequence in combination with Extension
      Primer

<400> SEQUENCE: 24
acgttggatg gctctttatt gtgaaagtat g                                        31

<210> SEQ ID NO 25
<211> LENGTH: 29
<212> TYPE: DNA
<213> ORGANISM: Artificial Sequence
<220> FEATURE:
<223> OTHER INFORMATION: TAG Sequence in combination with Extension
      Primer

<400> SEQUENCE: 25
acgttggatg ggtttgtgga aaacaaatg                                           29

<210> SEQ ID NO 26
<211> LENGTH: 30
<212> TYPE: DNA
<213> ORGANISM: Artificial Sequence
<220> FEATURE:
<223> OTHER INFORMATION: TAG Sequence in combination with Extension
      Primer
```

```
<400> SEQUENCE: 26
acgttggatg ggaatgggta actcttcttg                                    30

<210> SEQ ID NO 27
<211> LENGTH: 30
<212> TYPE: DNA
<213> ORGANISM: Artificial Sequence
<220> FEATURE:
<223> OTHER INFORMATION: TAG Sequence in combination with Extension
      Primer

<400> SEQUENCE: 27
acgttggatg tttctcaact gcctcaccac                                    30
```